(12) United States Patent
Eichman et al.

(10) Patent No.: US 8,765,100 B2
(45) Date of Patent: *Jul. 1, 2014

(54) TRANSMUCOSAL EFFERVESCENT

(75) Inventors: Jonathan D. Eichman, Ann Arbor, MI (US); John Hontz, Plymouth, MN (US); Rajendra K. Khankari, Maple Grove, MN (US); Sathasivan Indiran Pather, Plymouth, MN (US); Joseph R. Robinson, Madison, WI (US)

(73) Assignee: Cephalon, Inc., Frazer, PA (US)

( * ) Notice: Subject to any disclaimer, the term of this patent is extended or adjusted under 35 U.S.C. 154(b) by 111 days.

This patent is subject to a terminal disclaimer.

(21) Appl. No.: 12/429,475

(22) Filed: Apr. 24, 2009

(65) Prior Publication Data

US 2009/0202632 A1 Aug. 13, 2009

Related U.S. Application Data

(63) Continuation of application No. 09/661,693, filed on Sep. 14, 2000, now abandoned, which is a continuation of application No. 09/327,814, filed on Jun. 8, 1999, now Pat. No. 6,200,604, and a continuation of application No. 09/277,424, filed on Mar. 26, 1999, now abandoned.

(60) Provisional application No. 60/079,652, filed on Mar. 27, 1998.

(51) Int. Cl.
  *A01N 25/02* (2006.01)
  *A61K 9/12* (2006.01)
  *A61F 13/00* (2006.01)
  *A61K 9/20* (2006.01)
  *A61K 9/46* (2006.01)

(52) U.S. Cl.
  USPC ............... 424/43; 424/44; 424/434; 424/466; 424/464; 514/329

(58) Field of Classification Search
  USPC .............................. 424/44, 43, 434, 466, 464
  See application file for complete search history.

(56) References Cited

U.S. PATENT DOCUMENTS

| | | | |
|---|---|---|---|
| 1,262,888 A | 4/1918 | Preble et al. |
| 2,887,437 A | 5/1959 | Klioze et al. |
| 3,042,531 A | 7/1962 | Leal et al. |
| 3,131,123 A | 4/1964 | Masquelier |
| 3,577,490 A | 5/1971 | Welsh et al. |
| 3,888,976 A | 6/1975 | Mlkvy et al. |
| 3,961,041 A | 6/1976 | Nishimura et al. |
| 3,962,417 A | 6/1976 | Howell |
| 3,972,995 A | 8/1976 | Tsuk et al. |
| 4,147,768 A | 4/1979 | Schaffer et al. |
| 4,187,286 A | 2/1980 | Marcus |
| 4,289,751 A | 9/1981 | Windheuser |
| 4,370,160 A | 1/1983 | Ziemelis |
| 4,443,428 A | 4/1984 | Oshlack et al. |
| 4,493,848 A | 1/1985 | LaHann et al. |
| 4,503,031 A | 3/1985 | Glassman |
| 4,599,342 A | 7/1986 | Lahann |
| 4,613,497 A | 9/1986 | Chaukin |
| 4,639,368 A | 1/1987 | Niazi et al. |
| 4,671,953 A | 6/1987 | Stanley et al. |
| 4,687,662 A | 8/1987 | Schobel |
| 4,689,218 A | 8/1987 | Gazzaniga et al. |
| 4,717,723 A | 1/1988 | Sugden |
| 4,725,427 A | 2/1988 | Ashmead |
| 4,753,792 A | 6/1988 | Aberg |
| 4,756,710 A | 7/1988 | Bondi et al. |
| 4,853,211 A | 8/1989 | Kurobe et al. |
| 4,863,737 A | 9/1989 | Stanley et al. |
| 4,876,039 A | 10/1989 | Lo et al. |
| 4,940,588 A | 7/1990 | Sparks |
| 5,002,771 A | 3/1991 | Purkaystha et al. |
| 5,004,601 A | 4/1991 | Snipes |
| 5,028,411 A | 7/1991 | Callingham et al. |
| 5,053,396 A | 10/1991 | Blass |
| 5,055,306 A | 10/1991 | Barry |
| 5,073,374 A | 12/1991 | McCarty |
| 5,102,665 A | 4/1992 | Schaeffer |
| 5,102,666 A | 4/1992 | Acharya |
| 5,135,752 A | 8/1992 | Snipes |
| 5,178,878 A | 1/1993 | Wehling et al. |
| 5,223,264 A | 6/1993 | Wehling et al. |
| 5,234,957 A | 8/1993 | Mantelle |
| 5,288,497 A | 2/1994 | Stanley et al. |

(Continued)

FOREIGN PATENT DOCUMENTS

| | | |
|---|---|---|
| CA | 2211586 | 8/1996 |
| CA | 2218370 | 2/1997 |

(Continued)

OTHER PUBLICATIONS

Streisand et al. (Buccal absorption of fentanyl is pH-dependent in dogs', Anesthesiology, (Mar. 1995), 82 (3), pp. 759-64).*

(Continued)

*Primary Examiner* — Uma Ramachandran

(57) ABSTRACT

A pharmaceutical dosage form adapted to supply a medicament to the oral cavity for buccal, sublingual or gingival absorption of the medicament which contains an orally administerable medicament in combination with an effervescent for use in promoting absorption of the medicament in the oral cavity. The use of additional pH adjusting substance in combination with the effervescent for promoting the absorption of drugs is also disclosed.

7 Claims, No Drawings

(56) References Cited

U.S. PATENT DOCUMENTS

| | | | |
|---|---|---|---|
| 5,314,904 A | 5/1994 | Egidio et al. | |
| 5,387,420 A | 2/1995 | Mitchell | |
| 5,401,513 A | 3/1995 | Wehling et al. | |
| 5,445,827 A | 8/1995 | Fritsch et al. | |
| 5,458,879 A | 10/1995 | Singh et al. | |
| 5,464,632 A | 11/1995 | Cousins | |
| 5,468,504 A | 11/1995 | Schaeffer | |
| 5,501,861 A | 3/1996 | Makino | |
| 5,503,846 A | 4/1996 | Wehling et al. | |
| 5,550,861 A | 8/1996 | Chan et al. | |
| 5,559,096 A | 9/1996 | Edwards et al. | |
| 5,607,697 A | 3/1997 | Alkire et al. | |
| 5,624,687 A | 4/1997 | Yano et al. | |
| 5,626,866 A | 5/1997 | Ebert et al. | |
| 5,635,210 A | 6/1997 | Allen, Jr. et al. | |
| 5,646,151 A | 7/1997 | Kruse et al. | |
| 5,656,284 A | 8/1997 | Balkin | |
| 5,720,974 A | 2/1998 | Makino | |
| 5,785,989 A | 7/1998 | Stanley et al. | |
| 5,807,688 A | 9/1998 | Blackburn et al. | |
| 5,851,553 A | 12/1998 | Myers et al. | |
| 5,853,748 A | 12/1998 | New | |
| 5,900,252 A | 5/1999 | Calanchi et al. | |
| 5,952,004 A | 9/1999 | Rudnic et al. | |
| 5,958,455 A | 9/1999 | Roser et al. | |
| 5,958,458 A * | 9/1999 | Norling et al. | 424/490 |
| 6,034,085 A | 3/2000 | Joshi et al. | |
| 6,068,853 A | 5/2000 | Giannos et al. | |
| 6,071,539 A * | 6/2000 | Robinson et al. | 424/466 |
| 6,106,861 A | 8/2000 | Chauveau et al. | |
| 6,117,912 A | 9/2000 | Disanto | |
| 6,129,906 A | 10/2000 | Steventon | |
| 6,155,423 A | 12/2000 | Katzner et al. | |
| 6,171,617 B1 | 1/2001 | Gruber | |
| 6,190,697 B1 | 2/2001 | Gergely et al. | |
| 6,200,604 B1 | 3/2001 | Pather et al. | |
| 6,242,002 B1 | 6/2001 | Tritthart et al. | |
| 6,262,062 B1 | 7/2001 | Clemens | |
| 6,264,981 B1 | 7/2001 | Zhang et al. | |
| 6,284,274 B1 | 9/2001 | Merrill et al. | |
| 6,316,027 B1 | 11/2001 | Clarke et al. | |
| 6,326,360 B1 | 12/2001 | Kanazawa et al. | |
| 6,326,384 B1 | 12/2001 | Whittle et al. | |
| 6,350,470 B1 | 2/2002 | Pather et al. | |
| 6,368,625 B1 | 4/2002 | Siebert et al. | |
| 6,391,335 B1 | 5/2002 | Pather et al. | |
| 6,488,961 B1 | 12/2002 | Robinson et al. | |
| 6,509,036 B2 | 1/2003 | Pather et al. | |
| 6,576,250 B1 | 6/2003 | Pather et al. | |
| 6,641,838 B2 | 11/2003 | Pather et al. | |
| 6,680,071 B1 | 1/2004 | Johnson et al. | |
| 6,759,059 B1 | 7/2004 | Petterson et al. | |
| 6,761,910 B1 | 7/2004 | Petterson et al. | |
| 6,764,696 B2 | 7/2004 | Pather et al. | |
| 6,835,194 B2 | 12/2004 | Johnson et al. | |
| 6,974,590 B2 | 12/2005 | Pather et al. | |
| 7,670,617 B2 | 3/2010 | Pather et al. | |
| 7,858,121 B2 | 12/2010 | Moe et al. | |
| 7,862,832 B2 | 1/2011 | Moe et al. | |
| 7,862,833 B2 | 1/2011 | Moe | |
| 2001/0006677 A1 | 7/2001 | McGinty et al. | |
| 2001/0041165 A1 | 11/2001 | Katdare et al. | |
| 2002/0160991 A1 | 10/2002 | Shao | |
| 2003/0035839 A1 | 2/2003 | Hirsch | |
| 2004/0213855 A1 | 10/2004 | Petterson et al. | |
| 2005/0037072 A1 | 2/2005 | Pather et al. | |
| 2005/0042281 A1 | 2/2005 | Singh et al. | |
| 2005/0142197 A1 | 6/2005 | Moe et al. | |
| 2005/0142198 A1 | 6/2005 | Moe et al. | |
| 2005/0163838 A1 | 7/2005 | Moe | |
| 2005/0169989 A1 | 8/2005 | Moe et al. | |
| 2006/0292219 A1 | 12/2006 | Pather et al. | |
| 2007/0036853 A1 | 2/2007 | Agarwal et al. | |
| 2008/0131508 A1 | 6/2008 | Agarwal et al. | |
| 2009/0214442 A1 | 8/2009 | Agarwal et al. | |

FOREIGN PATENT DOCUMENTS

| | | |
|---|---|---|
| CA | 2254060 | 11/1997 |
| CA | 2326502 | 7/1999 |
| DE | 41 39 883 | 6/1993 |
| EP | 0 275 834 | 7/1986 |
| EP | 0 197 504 A1 | 10/1986 |
| EP | 0 354 973 B2 | 2/1990 |
| EP | 0 361 680 A2 | 4/1990 |
| EP | 0 396 335 | 11/1990 |
| EP | 0737473 | 10/1996 |
| EP | 0839526 | 5/1998 |
| EP | 1 062 952 A | 12/2000 |
| EP | 1 067 905 | 1/2001 |
| FR | 2 732 217 | 10/1996 |
| GB | 3160 | 0/1872 |
| GB | 1 212 704 | 11/1970 |
| GB | 2307857 A | 6/1997 |
| JP | 7-277959 | 10/1995 |
| NL | 7 302 521 | 8/1974 |
| TW | 36236 | 4/1981 |
| TW | 40484 | 12/1981 |
| TW | 40485 | 12/1981 |
| TW | 200611697 | 4/2006 |
| WO | WO 91/04757 * | 4/1991 |
| WO | WO 93/02662 | 2/1993 |
| WO | WO 95/07701 | 3/1995 |
| WO | WO 95/27482 A1 | 10/1995 |
| WO | WO 95/34291 A1 | 12/1995 |
| WO | WO 96/29993 A1 | 10/1996 |
| WO | WO 97/06786 | 2/1997 |
| WO | WO 97/17067 A1 | 5/1997 |
| WO | WO9718796 | 5/1997 |
| WO | WO 99/45934 A | 9/1999 |
| WO | WO 99/49842 | 10/1999 |
| WO | WO 00/59423 | 1/2000 |
| WO | WO 00/09093 A | 2/2000 |
| WO | WO0035418 | 6/2000 |
| WO | WO 00/57858 | 10/2000 |
| WO | WO 01/80822 | 11/2001 |
| WO | WO 2004/067004 | 8/2004 |
| WO | WO 2005/065318 | 7/2005 |
| WO | WO 2005/065319 | 7/2005 |

OTHER PUBLICATIONS

Chen et al. (Studies on formulations of fentanyl buccal adhesive tablets, Zhongguo Yiyao Gongye Zazhi, 1997, 28(3), 129-1311).*
Streisand et al. (Anesthesiology, 75, 223-229, 1991).*
*Cephalon Inc. and CIMA Labs Inc.*, v. *Barr Pharmaceuticals, Inc., and Barr Laboratories, Inc.*, Answer to Counterclaims, Case No. 08-cv-00455-JJF, Sep. 4, 2008.
Sterne, Kessler, Letter dated Sep. 17, 2008.
*Cephalon Inc. and CIMA Labs Inc.* v. *Watson Pharmaceuticals., Inc., and Watson Laboratories, Inc.*, Defendants' First Set of Rule 33 Interrogatories to Plaintiffs, C.A. No. 08-330-JJF, Sep. 18, 2008.
*Cephalon Inc. and CIMA Labs Inc.* v. *Watson Pharmaceuticals., Inc., and Watson Laboratories, Inc.*, Answer and Counterclaims, Case No. 3:08-cv-308-LRH-RAM, Oct. 14, 2008.
*Cephalon Inc. and CIMA Labs Inc.*, v. *Barr Pharmaceuticals, Inc., and Barr Laboratories, Inc.*, Complaint for Patent Infringement, Oct. 29, 2008.
*Cephalon Inc. and CIMA Labs Inc.* v. *Watson Pharmaceuticals., Inc., and Watson Laboratories, Inc.*, Answer to Counterclaims, Case No. 3:08-cv-00308-LHR-RAM, Nov. 3, 2008.
Sterne, Kessler, Letter dated Dec. 22, 2008.
*Cephalon Inc. and CIMA Labs Inc.*, v. *Barr Pharmaceuticals, Inc., and Barr Laboratories, Inc.*, Barr's First Set of Interrogatories to Cephalon, Inc. and CIMA Labs Inc., (Nos. 1-10) Case No. 08-cv-00455 (JJF), Dec. 23, 2008.
*Cephalon Inc. and CIMA Labs Inc.*, v. *Barr Pharmaceuticals, Inc., and Barr Laboratories, Inc.*, Barr's Responses and Objections to Plaintiffs Cephalon, Inc.'s and CIMA Labs Inc.'s First Set of Interrogatories (Nos. 1-10), Jan. 9, 2009.
*Cephalon Inc. and CIMA Labs Inc.* v. *Watson Pharmaceuticals., Inc. and Watson Laboratories, Inc.*, Defendants' Objections and Responses to First Set of Interrogatories, (Nos. 1-11), C.A. No. 08-330-SLR, Jan. 12, 2009.

(56) References Cited

OTHER PUBLICATIONS

*Cephalon Inc. and CIMA Labs Inc., v. Barr Pharmaceuticals, Inc., and Barr Laboratories, Inc.*, Plaintiffs' Response to Defendants' First Set of Interrogatories, (Nos. 1-10) Civil Action No. 08-455-SLR, Jan. 26, 2009.
*Cephalon Inc. and CIMA Labs Inc., v. Barr Pharmaceuticals, Inc., and Barr Laboratories, Inc.*, Answer, Affirmative Defenses and Counterclaims, Case No. 08-cv-810 SLR, Jan. 27, 2009.
*Cephalon Inc. and CIMA Labs Inc., v. Barr Pharmaceuticals, Inc.*, Barr Pharmaceuticals, LLC, as successor-in-interest to Barr Pharmaceuticals, Inc. and Barr Laboratories, Inc., Complaint for Patent Infringement, Jan. 30, 2009.
*Cephalon, Inc. and CIMA Labs Inc. v. Watson Pharmaceuticals., Inc., Watson Laboratories, Inc., and Watson Pharma, Inc.*, Amended Complaint for Patent Infringement, Civil Action No. 08-330 SLR, Feb. 4, 2009, Redacted.
*Cephalon Inc. and CIMA Labs Inc., v. Barr Pharmaceuticals, Inc., and Barr Laboratories, Inc.*, Barr's Responses and Objections to Plaintiffs Cephalon Inc.'s and CIMA Labs Inc.'s Second Set of Interrogatories (No. 11), Case No. 08-cv-00455 (SLR), Feb. 11, 2009.
*Cephalon Inc. and CIMA Labs Inc., v. Barr Pharmaceuticals, Inc., and Barr Laboratories, Inc.*, Answer to Counterclaims, Civil Action No. 08-810 SLR, Feb. 17, 2009.
*Cephalon Inc. and CIMA Labs Inc., v. Barr Pharmaceuticals, Inc.*, Barr Pharmaceuticals, LLC, as successor-in-interest to Barr Pharmaceuticals, Inc. and Barr Laboratories, Inc., Answer, Affirmative Defenses and Counterclaims, Case. No. 1:09-cv-00074-SLR, Feb. 23, 2009.
*Cephalon Inc. and CIMA Labs Inc., v. Barr Pharmaceuticals, Inc.*, Barr Pharmaceuticals, LLC, as successor-in-interest to Barr Pharmaceuticals, Inc. and Barr Laboratories, Inc., Answer to Counterclaims, Civil Action No. 09-074 SLR, Mar. 13, 2009.
*Cephalon Inc. and CIMA Labs Inc., v. Barr Pharmaceuticals, Inc., and Barr Laboratories, Inc.*, Plaintiffs' Supplemental Response to Defendants' First Set of Interrogatories (Nos. 1-10), Mar. 30, 2009.
*Cephalon, Inc. and CIMA Labs Inc. v. Watson Pharmaceuticals., Inc.*, Watson Laboratories, Inc., and Watson Pharma, Inc., Defendants' Supplemental Objections and Responses to Plaintiffs' First Set of Interrogatories, C.A. No. 08-330-SLR, Mar. 30, 2009.
*Cephalon, Inc. and CIMA Labs Inc. v. Watson Pharmaceuticals., Inc., Watson Laboratories, Inc., and Watson Pharma, Inc.*, Answer and Counterclaims to Amended Complaint, C.A. No. 08-330-SLR, Apr. 27, 2009, Redacted.
*Cephalon, Inc. and CIMA Labs Inc. v. Watson Pharmaceuticals., Inc., Watson Laboratories, Inc., and Watson Pharma, Inc.*, Plaintiffs' Response to Defendants' Invalidity Contentions, Civil Action No. 08-330-SLR, Apr. 29, 2009.
*Cephalon, Inc. and CIMA Labs Inc. v. Watson Pharmaceuticals., Inc., Watson Laboratories, Inc., and Watson Pharma, Inc.*, Defendants' Second Supplemental Objections and Responses to Plaintiffs' First Set of Interrogatories, C.A. 08-330-SLR, Apr. 29, 2009.
*Cephalon, Inc. and CIMA Labs Inc. v. Watson Pharmaceuticals., Inc., Watson Laboratories, Inc., and Watson Pharma, Inc.*, Answer to Counterclaims, C.A. No. 08-330 SLR, May 18, 2009.
Fish & Richardson, Letter dated May 29, 2009.
*Cephalon Inc. and CIMA Labs Inc., v. Barr Pharmaceuticals, Inc., and Barr Laboratories, Inc.*, Plaintiffs' Second Set of Interrogatories (Nos. 1-10) Civil Action No. 08-455-SLR, May 29, 2009.
Amended Complaint for Patent Infringement re: *Ceph et al. v. Watson et al.*, dated Jan. 16, 2009.
Answer, Affirmative Defenses and Counterclaims, *Ceph et al. v. Barr et al.*, dated Aug. 12, 2008.
Clinical Pharmacology FDA Submission, Clinical Pharmacology and Biopharmaceutics Reviews, NDAS 21-947, Fentanyl Buccal Tablet DFS, pp. 1-86, 31 pages withheld, 2006.
Complaint for Patent Infringement w/ Exhibits A & B, re: *Ceph et al. v. Watson et al.*, Jun. 2, 2008.
Complaint for Patent Infringement re: *Ceph et al. v. Watson et al.*, Jun. 3, 2008.
Complaint for Patent Infringement re: *Ceph et al. v. Barr et al.*, Jul. 22, 2008.
Eichman, Jonathan D., "Increased Drug Absorption Through Carbonation: Assessment of Biological Membranes", A thesis submitted in partial fulfillment of the requirements for the degree of Master of Science (Pharmaceutics) at the University of WI-Madison, (1995).
Eichman, Jonathan D., "Mechanistic Studies on Effervescent-Induced Permeability Enhancement", Pharmaceutical Research, vol. 15, No. 6, pp. 925-930, 1998.
Hagerstrom, Theses, "Polymer Gels as Pharmaceutical Dosage Forms: Rheological Performance and Physicochemical Interactions at the Gel-Mucus Interface for Formulations Intended for Mucosal Drug Delivery", Theses from Uppsala University, 3538—Polymer Gels as Pharmaceutical Dosage Forms, pp. 1-3, Sep. 7, 2004.
Impax Lab, Paragraph IV Certification Notice, dated Oct. 6, 2011.
International Search Report for PCT Application No. PCT/US00/07567, dated Jul. 5, 2000.
International Search Report for PCT Application No. PCT/US04/43703 dated Nov. 1, 2005.
Joint Claim Construction Chart by Cephalon and Sandoz dated Apr. 15, 2011.
Malpani, "Sodium Starch Glycolate", 13 pages, Jan. 5, 2010.
Notice of Paragraph IV Certification: Amendment to ANDA No. 202577 Fentanyl Citrate Buccal Tablets, (Flynn), re: Mylan et al. dated Sep. 28, 2011.
Notice of References re: U.S. Appl. No. 12/955,346, 2011.
Notification of Certification of Invalidity, Unenforceability and/or Non-Infringement for U.S. Patent Nos. 6,200,604 and 6,974,590, Letter from Watson dated Apr. 15, 2008.
Order for the Transcript of the Discussions and Rulings During the Teleconference dated Mar. 11, 2011.
U.S. Appl. No. 09/661,693, filed Sep. 14, 2000.
Physician's Desk Reference Actiq, pp. 1151-1155, 2004.
Physician's Desk Reference Kadian, pp. 569-573, 2005.
Portenoy et al., "Fentanyl Buccal Tablet (FBT) for Relief of Breakthrough Pain in Opioid-Treated Patients with Chronic Low Back Pain: A Randomized, Placebo-Controlled Study", Fentanyl Buccal Tablet for Breakthrough Pain, vol. 23(1), pp. 223-233, (2007).
Redacted Version 72 Letter to Thynge from Shaw re: Motion to Compel the Production of Navinta Formulation and Related Documents by Sandoz dated Feb. 17, 2011.
Redacted Version of 89 Letter Opening Brief in Support of Plaintiff's Motion to Stay Proceedings by Cephalon et al. dated Apr. 5, 2011.
Redacted Version of 105 Reply Brief. Plaintiffs Cephalon et al., Motion to Stay Proceedings. (Attchmnts #1 Ex. A), dated May 2, 2011.
Redacted Version of 107 Plaintiff's Claim Construction Opening Brief dated May 2, 2011.
Redacted Version of 108 Declaration of Oakes in Support of Plaintiffs' Opening Claim Construction Brief by Plaintiffs dated May 2, 2011.
Redacted Letter to Mag. J. Thynge, FR McCann re discovery extension—Proposed Order, C.A. No. 10-123-SLR/MPT, dated Mar. 29, 2011.
Search Query of Fentanyl, 2012.
Telephone Conversation held on Apr. 24, 2010 re: Apr. 19, 2010, Apr. 20, 2010 and Apr. 21, 2010 re: 04815716.8 for auxiliary dated Apr. 27, 2010.
U.S. Appl. No. 10/936,185, Pather et al.
Alternative Routes of Drug Administration—Advantages and Disadvantages (Subject Review), American Academy of Pediatrics Committee on Drugs, Pediatrics, vol. 100, No. 1, pp. 143, 147, Jul. 1997.
Amighi, K.; Timmermans, J.; Puigdevall, J.; Baltes, E.; Moes, A.J.; "Peroral Sustained-Release Film-Coated Pellets as a Means to Overcome Physiochemical and Biological Drug-Related Problems". I In Vitro Development and Evaluation, Drug Development and Industrial Pharmacy, vol. 24, No. 6, pp. 509-515 (1998).
Audus, K.L., "Buccal Epithelial Cell Cultures as a Model to Study Oral Mucosal Drug Transport and Metabolism" *Oral Mucosal Drug Delivery*, Ch 6, pp. 101-115.
Audus, K.L. et al., "The Use of Cultured Epithelial and Endothelial Cells for Drug Transport and Metabolism Studies", Pharmaceutical Research, vol. 7, No. 5, p. 435, 1990.

(56) References Cited

OTHER PUBLICATIONS

Aungst, B.J., "Oral Mucosal Permeation Enhancement: Possibilities and Limitations" *Oral Mucosal Drug Delivery*, Ch. 4, pp. 65-81 (1996).
Berko, S; Regdon Jun, G.; Eros, I.; "Influence of pH Change on Drug Release from Rectal Suppositories", Die Pharmazie, vol. 55, p. 324, Apr. 2000, Govi-Verlag Pharmazeutischer Verlag GmbH, Eschborn.
Bredenberg, Susanne, "New Concepts in Administration of Drugs in Tablet Form", Thesis (Comprehensive Summaries of Uppsala Dissertations from the Faculty of Pharmacy 287) 2003.
*Cephalon Inc. and CIMA Labs Inc. v. Watson Pharmaceuticals., Inc., and Watson Laboratories, Inc.*, complaint for patent infringement, Civil Action #08-330, 2009.
*Cephalon Inc. and CIMA Labs Inc., v. Barr Pharmaceuticals, Inc., and Barr Laboratories, Inc.*, complaint for patent infringement, 2008.
*Cephalon Inc. and CIMA Labs Inc. v. Barr Pharmaceuticals, Inc., and Barr Laboratories, Inc.*, Case No. 08-cv-00455 (UNA), answer, affirmative defenses and counterclaims, 2008.
*Cephalon v. Watson*, Para. IV—Redacted, 2011.
Chen et al., "Studies on formulations of fentanyl buccal adhesive tablets", Zhongguo Yiyao Gongye Zazhi, 1997, 28(3), 129-131.
Conine, James W., Special Tablets in Pharmaceutical Dosage Forms, Tablets, vol. 1, p. 329 (Herbert A Lieberman et al. eds. 1989).
DeGrande et al., "Specialized Oral Mucosal Drug Delivery Systems: Patches" *Oral Mucosal Drug Delivery*, Ch 12, pp. 285-313 (1998).
Eichman, J.D., Thesis "Mechanistic Studies on Effervescent-Induced Permeability Enhancement" (catalogued at the University of Wisconsin-Madison on Sep. 18, 1998) (on file with the University of Wisconsin-Madison).
Eichman, J.D. and Robinson, J.R., "Mechanistic Studies on Effervescent-Induced Permeability Enhancement", Pharm. Res. 15(6) pp. 925-930(1998).
Giannos, S.A.; Dinh, S.M.; Berner, B.; "Temporally Controlled Drug Systems: Coupling of pH Oscillators with Membrane Diffusion", Journal of Pharmaceutical Sciences, vol. 84, No. 5, pp. 539-543, May 1995.
Hagerstrom, Helene, "Polymer Gels as Pharmaceutical Dosage Forms" Thesis (Comprehensive Summaries of Uppsala Dissertations from the Faculty of Pharmacy 293) 2003.
Hessel, P.G., et al., "A Comparison of the availability of prochlorperazine following i.m. buccal and oral administration", International Journal of Pharmaceutics, vol. 52, Issue 2, p. 159-164, Jun. 1, 1989.
http://chemical1and21.com/industrialchem/inorganic/SODIUM%20SULPHATE.htm, Sodium Sulphate, 2 pages, 2012.
Kellaway, I.W. and Warren, S.J., "Mucoadhesive Hydrogels for Buccal Delivery" *Oral Mucosal Drug Delivery*, Ch. 10, pp. 221-237 (!996).
Lieberman, Herbert A., ed., "Pharmaceutical Dosage Forms—Tablets", vol. 1, $2^{nd}$. ed., pp. 372-376, (1989).
Nishimura et al., "Dosage Form Design for Improvement of Bioavailability of Levodopa VI: Formulation of Effervescent Enteric-Coated Tablets", J. Pharm Sci. 73(7), 942-46 (1984).
Pather et al, "Buccal Delivery—Enhanced Buccal Delivery of Fentanyl Using the Oravescent Drug Delivery System", Drug Delivery Tech., vol. 1, No. 1, Oct. 2001.
Ranade, V.V.; "Drug Delivery Systems Part 5B. Oral Drug Delivery", The Journal of Clinical Pharmacology, vol. 31, pp. 98-115, Feb. 1991.
Rassing, R., "Specialized Oral Mucosal Drug Delivery Systems: Chewing Gum" *Oral Mucosal Drug Delivery*, Ch. 13, pp. 319-353 (1996).
Rathbone et al., "In Vivo Techniques for Studying the Oral Mucosal Absorption Characteristics of Drugs in Animals and Humans," Oral Mucosal Drug Delivery, Ch. 7, pp. 121-151 (1996).
Rathbone et al., "Systemic Oral Mucosal Drug Delivery and Delivery Systems", *Oral Mucosal Drug Delivery*, Ch. 11, pp. 241-275 (1996).
Rowe et al., Handbook of Pharmaceutical Excipients, 2006, Fifth Edition, pp. 758-759.
Sasahara et al., "Dosage Form Design for Improvement of Bioavailability of Levodopa II: Bioavailability of Marketed Levodopa Preparations in Dogs and Parkinsonian Patients" J. Pharm. Sci. 69(3), pp. 261-265 (1980).
Sasahara et al., "Dosage Form Design for Improvement of Bioavailability of Levodopa III: Influence of Dose on Pharmacokinetic Behavior of Levodopa in Dogs and Parkinsonian Patients" J. Pharm. Sci., 69(12), pp. 1374-1378 (1980).
Sasahara et al., "Dosage Form Design for Improvement of Bioavailability of Levodopa V: Absorption and Metabolism of Levodopa in Intestinal Segments of Dogs" J. Pharm. Sci., 70(10), 1157-60 (1981).
Sasahara et al., "Dosage Form Design for Improvement of Bioavailability of Levodopa IV: Possible Causes of Low Bioavailability of Oral Levodopa in Dogs", J. Pharm Sci., 70(7) pp. 730-733 (1981).
Schenkels et al., "Salivary Mucins: Their Role in Oral Mucosal Barrier Function and Drug Delivery" *Oral Mucosal Drug Delivery*, Ch. 9, pp. 191-211 (1996).
Sorasuchart, W.; Wardrop, J.; Ayers, J., "Drug Release from Spray Layered and Coated Drug-Containing Beads: Effects of pH and Comparison of Different Dissolution Methods", Drug Development and Industrial Pharmacy, vol. 25, No. 10, pp. 1093-1098 (1999).
Soskolone, W.A. and Friedman, M., "Intra-periodontal Pocket Drug Delivery Systems" *Oral Mucosal Drug Delivery*, Ch. 14, pp. 359-373 (1996).
Squire, C.A. and Wertz, P.W., "Structure and Function of the Oral Mucosa and Implications for Drug Delivery" *Oral Mucosal Drug Delivery*, Ch. 1, pp. 1-19.
Stanley et al., "Novel Delivery Systems: Oral Transmucosal and Intranasal Transmucosal", Journal of Pain and Symptom Management, vol. 7, No. 3 pp. 163-171, 1992.
Sterne, Kessler, Letter dated Jun. 9, 2008.
Sterne, Kessler, Letter dated Jun. 27, 2008.
Streisand (Anesthesiology, 1991, 75(2), 223-9).
Streisand et al., "Buccal absorption of fentanyl is pH-dependent in dogs", Anesthesiology, (Mar. 1995), 82(3), pp. 759-764.
Streubel, A.; Siepmann, J.; Dahevsky, A.; Bodmeier, R., "pH-Independent Release of a Weakly Basic Drug from Water-Insoluble and -Soluble Matrix Tablets," Journal of Controlled Release, vol. 67, pp. 101-110 (2000).
The Alcohol and Other Drug Thesaurus, National Institute of Health, National Institute on Alcohol Abuse and Alcoholism (Third Edition, 2000, U.S. Dept. of Health and Human Services).
Weatherell et al., "The Flow of Saliva and its Influence on the Movement, Deposition, and Removal of Drugs Administered to the Oral Cavity", *Oral Mucosal Drug Delivery*, Ch. 8, pp. 157-187 (1996).
Weinberg et al., "Sublingual absorption of selected opioid analgesics", Clinical Pharmacology and Therapeutics, Sep. 1988, 44(3) pp. 335-342.
Wertz et al., "Biochemical Basis of the Permeability Barrier in Skin and Oral Mucosa",*Oral Mucosal Drug Delivery*, Ch. 2, pp. 27-41 (1996).
Zhang H. and Robinson J.R., "In Vitro Methods for Measuring Permeability of the Oral Mucosa" *Oral Mucosal Drug Delivery*, Ch. 5 pp. 85-97 (1996).
Zhang H. and Robinson J.R., "Routes of Drug Transport Across Oral Mucosa" *Oral Mucosal Drug Delivery*, Ch. 3, pp. 51-61 (1996).
Altomare, E. et al., "Bioavailability of a new effervescent tablet of ibuprofen in healthy volunteers," *Eur. J. Clin. Pharmacol.* 52:505-506 (1997).
Coluzzi et al., "Breakthrough Cancer Pain: A Randomized Trial Comparing Oral Transmucosal Fentanyl Citrate (OTFC®) and Morphine Sulfate Immediate Release (MSIR®)," *Pain* 91:123-130 (2001).
Darwish, M. et al., "Pharmacokinetics and Dose Proportionality of Fentanyl Effervescent Buccal Tablets in Healthy Volunteers," *Clin. Pharmacol.* 44(12): 1279-1286 (2005).
Darwish, M. et al. "Relative Bioavailability and Dose Proportionality of a Novel Effervescent Form of Fentanyl in Healthy Volunteers," *Anesthesiology* 103: A790 (2005).
Darwish, M. et al., "Absolute and Relative Bioavailability of Fentanyl Buccal Tablet and Oral Transmucosal Fentanyl Citrate," *J. Clin. Pharmacol.* 47:343-350 (2007).

(56) References Cited

OTHER PUBLICATIONS

Eichmann, Jonathan D., "Mechanistic Studies in Effervescent-Induced Permeability Enhancement," Dissertation, University of Wisconsin-Madison, catalogued Sep. 18, 1998.
Eichman, J.D. et al., "The influence of in-vivo carbonation on GI physiological processes and drug permeability," *Eur. J. Pharmaceutics and Biopharmaceutics* 44:33-38 (1997).
English Abstract for FR 2 732 217 dated Oct. 4, 1996, Derwent Week 199645.
English Abstract for DE 41 39 883 dated Jun. 3, 1993, Derwent Week 199323.
English Abstract for NL 7302521 dated Aug. 27, 1974, Derwent Week 197437.
European Communication from European Patent Office, European Patent Application No. 04 815 715.0, dated Mar. 28, 2008.
European Search Report for European Patent Application No. EP 00 91 9523 dated Apr. 29, 2002.
European Search Report for European Patent Application No. EP 04 81 5715 dated Nov. 14, 2007.
European Search Report for European Patent Application No. EP 00 92 6341 dated Nov. 23, 2005.
Fentora® (fentanyl buccal tablet) label, Oct. 2007 (9 pages).
Harris, D. et al. "Drug Delivery via the Mucous Membranes of the Oral Cavity," *Journal of Pharmaceutical Sciences*, 81(1): 1-10 (1992).
In re Wada and Murphy, Board of Patent Appeals and Interferences, Appeal 2007-3733 (Jan. 14, 2008) (9 pages).
International Search Report for PCT Application No. PCT/US04/43703, dated Nov. 1, 2005.
Kramer, TH et al. "Pharmacodynamic Model of the Effects of Morphine and Morphine-6-Glucoronide During Patient-Controlled Analgesia," *Clinical Pharmacology & Therapeutics*, 59(2), p. 132 (1996).
Labroo, RB et al. "Fentanyl Metabolism by Human Hepatic and Intestinal Cytochrome P450 3A4: Implications for Interindividual Variability in Disposition, Efficacy, and Drug Interactions," *Drug Metabolism and Disposition*, 25(9): 1072-1080 (1997).
Nishimura, K. et al. "Dosage Form Design for Improvement of Bioavailability of Levodopa VI: Formulation of Effervescent Enteric-Coated Tablets," *Journal of Pharmaceutical Sciences*, 73(7): 942-946 (1984).
Palmisano, BW Clinical Review of Fentanyl Oralet (oral transmucosal fentanyl citrate), NDA Application No. 20-195/S-002, dated Feb. 26, 1996.
Pather, SI et al. "Enhanced Buccal Delivery of Fentanyl Using the OraVescent Drug Delivery System," *Drug Delivery*, 1(1), Oct. 2001.
Portenoy, RK et al. "Breakthrough Pain: Definition, Prevalence and Characteristics," *Pain*, 41: 273-281 (1990).
Reisine, T. et al., "Opioid Analgesics and Antagonists", in Hardman, J.G. et al., editors. Goodman and Gilman's Pharmacologic Basis of Therapeutics. 9th rev. ed. New York: McGraw Hill, pp. 521-555, 1996.
Scott, JC et al. "EEG Quantitation of Narcotic Effect: The Comparative Pharmacodynamics of Fentanyl and Alfentanil," *Anesthesiology*, 62: 234-241 (1985).
Stanley, TH et al. "Novel Delivery Systems: Oral Transmucosal and Intranasal Transmucosal," *Journal of Pain and Symptom Management*, 7(3): 163-171 (1992).
Report on Filing of an Action, Docket No. 08cv330, dated Jun. 2, 2008.
Watson Pharmaceuticals Motion to Dismiss Pursuant to Fed. R. Civ. P. 12(b)(6) and (7), C.A. No. 08-330-JJF, dated Jul. 15, 2008.
Watson Labs Motion to Dismiss Pursuant to Fed. R. Civ. P. 12(b)(6) and (7), C.A. No. 08-330-JJF, dated Jul. 15, 2008.
Redacted Watson Labs Opening Brief in support of Motion to Dismiss, C.A. No. 08-330-JJF, dated Jul. 22, 2008.
Redacted Watson Pharmaceuticals Opening Brief in support of Motion to Dismiss, C.A. No. 08-330-JJF, dated Jul. 22, 2008.
Civil Cover *Cephalon* v *Sandoz*, dated Feb. 16, 2010.
Exhibit A—6,200,604 Patent submitted with Complaint *Cephalon* v *Sandoz*, dated Feb. 16, 2010.
Exhibit B—6,974,590 Patent submitted with Complaint *Cephalon* v *Sandoz*, dated Feb. 16, 2010.
Complaint *Cephalon* v *Sandoz*, dated Feb. 16, 2010.
Redacted Watson Defendants Opening Brief in support of Motion to Dismiss—Amended Complaint, C.A. No. 08-330-SLR, dated Feb. 20, 2009.
Redacted Declaration of Park in support of Watson in support of Motion to Dismiss—Amended Complaint—Exhibits 1-30, C.A. No. 08-cv-00330-SLR, dated Feb. 20, 2009.
Redacted Watson Labs Reply Brief in support of Motion to Dismiss, C.A. No. 08-330-SLR, dated Feb. 20, 2009.
Redacted Watson Pharmaceutical Reply Brief in support of Motion to Dismiss, C.A. No. 08-330-SLR, dated Feb. 20, 2009.
Redacted Brief in Opposition to Watson Pharmaceuticals Motion to Dismiss—Amended Complaint, C.A. No. 08-330-SLR, dated Mar. 23, 2009.
Oakes Declaration in support of Opposition to Watson Pharmaceuticals Motion to Dismiss—Amended Complaint, C.A. No. 08-330-SLR, dated Mar. 23, 2009.
Order Denying Motion to Dismiss, C.A. No. 08-330-SLR, dated Apr. 3, 2009.
Redacted Watson Defendants Reply Brief in support of Motion to Dismiss—Amended Complaint, C.A. No. 08-330-SLR, dated Apr. 1, 2009.
Redacted Park Declaration in support of Watson Reply in support of Motion to Dismiss—Amended Complaint, C.A. No. 08-cv-00330-SLR, dated Apr. 1, 2009.
Joint Claim Construction Statement C.A. No. 08-330-SLR, dated Feb. 12, 2010.
Notice Consent and Reference to a Magistrate, C.A. No. 10-cv-00123-UNA, Filed Feb. 16, 2010.
Cephalon Corporate Disclosure Statement, dated Feb. 16, 2010.
CIMA Corporate Disclosure Statement, dated Feb. 16, 2010.
Report on the Filing or Determination of an Action Regarding a Patent or Trademark, C.A. No. 10-cv-00123-UNA, Filed Feb. 16, 2010.
Proof of Service, US District Court for the District of Delaware, dated Feb. 17, 2010.
Sandoz Summons in a Civil Action dated Feb. 17, 2010.
Stipulation and Order to Ext Time re Answer to Complaint, C.A. No. 10-123-SLR, dated Mar. 10, 2010.
Text Order Granting Stipulation to Extend Time to Answer, dated Mar. 11, 2010.
Redacted Watson Opening Claim Construction Brief, Mar. 5, 2010.
Redacted Fineman Declaration in support of Watson Opening Construction Brief, Mar. 5, 2010.
Redacted Plaintiffs Consolidated Opening Markman Brief, Mar. 5, 2010.
Sandoz Answer, Defense, Counterclaims, C.A. No. 10-00123-SLR, dated Mar. 22, 2010.
Sandoz Corporate Disclosure Statement, C.A. No. 10-00123-SLR, dated Mar. 22, 2010.
Sandoz Pro Hac Vice Motion—Gargano of McDermott, C.A. No. 10-00123-SLR, dated Mar. 18, 2010.
Sandoz Pro Hac Vice Motion—Garcha-Dolkas-Chang-Boyle of McDermott, C.A. No. 10-00123-SLR, dated Mar. 23, 2010.
Text Order re Pro Hac Admission of McDermott Attorneys for Sandoz, dated Mar. 31, 2010.
Redacted Watson Pharmaceuticals Rebuttal Markman Brief, dated Mar. 30, 2010.
Redacted Cephalon Rebuttal Markman Brief, dated Mar. 30, 2010.
Redacted Cephalon Reply in support of Motion to Modify Protective Orders, dated Apr. 1, 2010.
Answer to Counterclaims, Civil Action No. 10-330-SLR, dated Apr. 15, 2010.
Order Setting Scheduling Teleconference, Civil Action No. 10-123-SLR, dated Apr. 20, 2010.
Redacted Pretrial Order, Civil Action No. 08-330-SLR, dated Apr. 26, 2010.
Redacted Plaintiffs Brief in Opposition to Defendants Motion to Exclude Certain CO2 Testing, C.A. No. 08-330-SLR, Apr. 23, 2010.
Proposed Scheduling Order, C.A. No. 10-123-SLR, May 11, 2010.
Order re Teleconference—Court Docket Error, dated May 11, 2010.

(56) References Cited

OTHER PUBLICATIONS

Redacted Watson Answering Brief in Opposition to Motion to Modify Protective Orders, dated Mar. 15, 2010.
Final Proposed Scheduling Order, C.A. No. 10-123-SLR, dated May 20, 2010.
Order re Teleconference—Court Docket Error, dated May 24, 2010.
Notice of Service re Plaintiffs Initial Disclosures, Civil Action No. 10-330-SLR, dated May 25, 2010.
Notice of Service re Defendants Initial Disclosures, C.A. No. 10-123-SLR, dated May 25, 2010.
Order Regarding Discovery Matters, C.A. No. 10-123-SLR-LPS, dated Jun. 3, 2010.
Scheduling Order Entered, e-mail Jun. 3, 2010.
Redacted Plaintiffs Opening Post-Trial Brief, dated Jun. 29, 2010.
Redacted Watson Opening Post-Trial Brief, dated Jun. 29, 2010.
Order Scheduling ADR Teleconference, .A. No. 10-123-SLR-LPS, dated Jul. 20, 2010.
Stipulated Amendment to Scheduling Order re Doc Production, .A. No. 10-123-SLR, dated Jul. 29, 2010.
Plaintiffs Responsive Post-Trail Brief on Validity, dated Jul. 30, 2010.
Booker Declaration in support of Motion Responsive Post-Trial Brief on Validity—Exhibits 1-5, dated Apr. 20, 2010.
Order Regarding Discovery Matters, C. A. No. 10-123-SLR/MPT, dated Aug. 5, 2010.
Order Scheduling ADR Teleconference, C. A. No. 10-123-SLR/MPT, dated Aug. 5, 2010.
Redacted Defendants Responsive Post-Trial Brief, dated Jul. 30, 2010.
Redacted Watson Motion to Strike Expert Testimony, dated Jul. 30, 2010.
Redacted Declaration of Bryan Braunel re Motion to Strike Exp Testimony, dated Aug. 11, 2010.
Order Rescheduling ADR Teleconference, C. A. No. 10-123-SLR/MPT, dated Aug. 13, 2010.
Redacted Watson Motion to Exclude CO2 Testing, dated Apr. 9, 2010.
Redacted Plaintiffs Opposition to Motion to Strike, dated Aug. 10, 2010.
Redacted Booker Declaration in support of Opposition to Motion to Strike with Ex A and B, dated Aug. 16, 2010.
Redacted Plaintiffs Reply Post-Trial Brief—corrected, dated Aug. 13, 2010.
Redacted Booker Declaration in support of Reply Post Trial Brief with Ex 1 and 2, dated Aug. 13, 2010.
Redacted Post-Trial Brief of Watson, dated Aug. 13, 2010.
Cephalon Notice of Service re 1st Set Interrogatories and Request for Production of Documents to Sandoz, dated Aug. 30, 2010.
2nd Stipulated Amendment to Scheduling Order re Doc Production, Civil Action No. 10-123-SLR, dated Aug. 30, 2010.
Order Scheduling ADR Teleconference—Sep. 22, 2010, C. A. No. 10-123-SLR/MPT, dated Aug. 31, 2010.
Sandoz Notice of Service re 1st Set Interrogatories and Request for Production of Documents to Cephalon, Civil Action No. 10-123-SLR, dated Aug. 31, 2010.
Cephalon Notice of Entry of Compton, Civil Action No. 10-123-SLR, dated Sep. 1, 2010.
ORDER setting Teleconference with MJ Thynge, C. A. No. 10-123-SLR/MPT, dated Sep. 22, 2010.
Redacted Corrected Watson Reply Post Trial Brief, Sep. 10, 2010.
Stipulated Amendment to SO re Doc Production and Claim Terms Exchange, Civil Action No. 10-123-SLR, dated Oct. 1, 2010.
Text Order Granting Stipulated Amendment to Scheduling Order, e-mail dated Oct. 5, 2010.
Cephalon Notice of Service re Responses and Objections to Sandoz 1st Interrogatories and Request for Production of Documents, Civil Action No. 10-123-SLR, dated Oct. 12, 2010.
Sandoz Notice of Service re Responses and Objections to Cephalon 1st Interrogatories and Request for Production of Documents, Civil Action No. 10-123-SLR, dated Oct. 12, 2010.
Sandoz Notice of Service, Civil Action No. 10-123-SLR, dated Oct. 18, 2010.
Cephalon Notice of Deposition to Sandoz, Civil Action No. 10-123-SLR, dated Oct. 18, 2010.
Order Setting Mediation Conference, C. A. No. 10-123-SLR/MPT, dated Oct. 25, 2010.
Cephalon Notice of Deposition to of Alison Sherwood, Civil Action No. 10-123-SLR, dated Oct. 25, 2010.
Cephalon Notice of Deposition to of Ellen Camos, Civil Action No. 10-123-SLR, dated Oct. 25, 2010.
Cephalon Notice of Deposition to of Indranil Nandi, Civil Action No. 10-123-SLR, dated Oct. 25, 2010.
Sandoz Notice of Subpoenas to Lerner David, Civil Action No. 10-123-SLR, dated Oct. 26, 2010.
Cephalon Notice of Subpoena to Navinta LLC, Civil Action No. 10-123-SLR, dated Oct. 26, 2010.
Sandoz Notice of Subpoena to Univ of Wisconsin-Madison, Civil Action No. 10-123-SLR, dated Oct. 27, 2010.
Sandoz Notice of Service re 2nd Notice to CIMA and Cephalon, Civil Action No. 10-123-SLR, dated Oct. 29, 2010.
Sandoz Notice of Subpoena to Jason Garbell Civil Action No. 10-123-SLR, dated Oct. 29, 2010.
Cephalon Subpoena Executed re Navinta Civil Action No. 10-123-SLR, dated Oct. 26, 2010.
Cephalon Notice of Service re Responses and Objections to Sandoz Notice of Deposition, Civil Action No. 10-123-SLR, dated Nov. 1, 2010.
Plaintiffs Notice of Service, Civil Action No. 10-123-SLR, dated Nov. 5, 2010.
Cephalon Notice of Service re Supplemental Responses to 1st Set of Interrogatories—Nos .3 and 5, Civil Action No. 10-123-SLR, dated Nov. 12, 2010.
Sandoz Notice of Service Objections to Cephalon Subpoena to Navinta, Civil Action No. 10-123-SLR, dated Nov. 17, 2010.
Sandoz Not of Subpoenas to Anesta-Coleman-Zhang ,Civil Action No. 10-123-SLR, dated Nov. 18, 2010.
Notice of Service re Responses and Objections Sandoz Subpoena to Anesta, Civil Action No. 10-123-SLR, dated Nov. 24, 2010.
Notice of Service re Responses and Objections Sandoz Subpoena to Dennis Coleman, Civil Action No. 10-123-SLR, dated Nov. 24, 2010.
Sandoz Notice of Service re Responses and Objections to Notice of Deposition, Civil Action No. 10-123-SLR, dated Dec. 1, 2010.
Cephalon and CIMA Notice of Service re Responses and Objections to Sandoz 2nd Notice of Deposition, Civil Action No. 10-123-SLR, dated Dec. 6, 2010.
Order Setting Continued Mediation Conference, C. A. No. 10-123-SLR/MPT, dated Dec. 10, 2010.
Cephalon Amended Notice of Deposition of Alison Sherwood, Civil Action No. 10-123-SLR, dated Dec. 29, 2010.
Proposed Stipulated Protective Order, Civil Action No. 10-123-SLR, dated Jan. 6, 2011.
Signed Protective Order, e-mail Jan. 7, 2011.
Fourth Stipulated Amendment to Scheduling Order, Civil Action No. 10-123-SLR, dated Jan. 14, 2011.
Cephalon Notice of Service re Supplemental Responses-Objections to Sandoz Notice of Deposition, Civil Action No. 10-123-SLR, dated Jan. 19, 2011.
Text Order Granting 4th Stip Amendment to Schedule Order, e-mail dated Jan. 19, 2011.
Redacted Plaintiffs Brief in support of Motion to Strike Defendants Not of Subsequent Authority, dated Jan. 13, 2011.
Redacted Booker Declaration in support of plaintiffs Motion to Strike, dated Jan. 13, 2011.
Redacted Defendants Answering Brief in Opposition to Mot to Strike 2011.
Redacted Gwinn Declaration in support of Def Answering Brief re Motion to strike, dated Jan. 18, 2011.
Redacted Suzuki Declaration in support of Def Answering Brief re Motion to strike, dated Jan. 18, 2011.
Order Setting Teleconference to Discuss Feb. 7, 2011 Mediation, C. A. No. 10-123-SLR/MPT, dated Jan. 31, 2011.
Email to Judge Thynge fr Marsden re parties availability for mediation, email dated Feb. 1, 2011.

(56) References Cited

OTHER PUBLICATIONS

Order Setting Teleconference re Dates for Mediation, C. A. No. 10-123-SLR/MPT, dated Feb. 2, 2011.
Order Setting Teleconference re Navinta Discovery Issue, C. A. No. 10-123-SLR/MPT, dated Feb. 11, 2011.
Redacted Defendants Mot ionto Vacate Oct. 28, 2010 Order, dated Jan. 19, 2011.
Redacted Boyer Declaration in support of Motion to Vacate w Exhibit 1, dated Feb. 3, 2011.
Redacted Suzuki Declaration in support of Motion to Vacate w—Exhibits 1-3, dated Jan. 19, 2011.
Redacted Plaintiffs Reply in support of Motion to Strike w—Exhibits 1-3, dated Jan. 28, 2011.
Redacted Plaintiffs Opposition to Defendants Motion to Vacate, dated Jan. 28, 2011.
Redacted Campbell Declaration in support of Plaintiffs to Defendants Motion to Vacate, dated Jan. 28, 2011.
Redacted Bradway Declaration in support of Plaintiffs Opposition to Defendants Motion to Vacate, dated Jan. 28, 2011.
Cephalon Notice of Deposition of Sunil Vandse, C. A. No. 10-123-SLR, dated Feb. 8, 2011.
Cephalon Notice of Deposition of Matthew Bohlman C. A. No. 10-123-SLR, dated Feb. 11, 2011.
Cephalon Notice of Service re 3rd Supplemental Responses and Objections to Sandoz 1st Interrogatories, C. A. No. 10-123-SLR, dated Feb. 11, 2011.
Redacted Sandoz Reply re Motion to Vacate, dated Feb. 3, 2011.
Redacted Boyer Declaration in support of Reply to Motion to Vacate, dated Feb. 3, 2011.
Order Setting Mediation Conference Mar. 23, 2011, C. A. No. 10-123-SLR, dated Feb. 14, 2011.
Sandoz Notice of Service re 3rd Supplemental Responses and Objections to Cephalon 1st Interrogatories, C. A. No. 10-123-SLR, dated Feb. 14, 2011.
Redacted Ltr to Mag J Thyne fr Marsden re discovery dispute—Exhibits A-K, dated Feb. 16, 2011.
Redacted Ltr to Mag J Thyne fr Marsden re discovery dispute, dated Feb. 9, 2011.
Cephalon Notice of Deposition of Jessica Martori, C. A. No. 10-123-SLR, dated Feb. 16, 2011.
Redacted Letter to Mag J Thyne fr Shaw re discovery dispute—Exhibits A-C, dated Feb. 17, 2011.
Redacted Letter to Mag J Thyne fr Shaw re discovery dispute , dated Feb. 10, 2011.
Redacted Letter to Mag J Thyne fr Shaw re Cephalon mot to compel Navinta-related docs, dated Feb. 15, 2011.
Civil Cover Sheet, *Cephalon and CIMA*, v . *Mylan Pharmaceuticals, and Mylan, Inc.* dated Feb. 24, 2011.
Complaint Mylan Pharmaceuticals and Mylan, Inc. w—Exhibits, dated Feb. 25, 2011.
Notice of Availability of Magistrate, dated Feb. 24, 2011.
Cephalon Disclosure Statement, dated Feb. 24, 2011.
CIMA Disclosure Statement, dated Feb. 24, 2011.
Supplemental Info for ANDA Patent Cases, dated Feb. 24, 2011.
Report on the Filing or Determination of an Action Regarding a Patent or Trademark, C.A. No. 11-cv-164, Filed Feb. 24, 2011.
Plaintiffs Notice of Service re Opening Expert Reports, C. A. No. 10-123-SLR, dated Feb. 23, 2011.
Defendant Notice of Service re Expert Report, C. A. No. 10-123-SLR, dated Feb. 28, 2011.
Order Setting Teleconference re Discovery Issue, C. A. No. 10-123-SLR/MPT, dated Mar. 8, 2011.
Executed Summons re Mylan Pharm—Served Feb. 25, 2011, US District Court of Delaware, 2011.
Executed Summons re Mylan Pharm—Served Feb. 25, 2012, dated Mar. 2, 2011.
Redacted Letter to Mag J Thynge fr Marsden—Att 1-6, dated Mar. 10, 2011.
Redacted Letter to Mag J Thynge fr Marsden re pending motion, dated Mar. 3, 2011.
Order—teleconference Transcript Stands as Order of Court re Navinta Discovery, C. A. No. 10-123-SLR/MPT, dated Mar. 11, 2011.
Opinion, *Cephalon Inc.* v. *Watson Pharma. Inc.*, C.A. No. 08-330-SLR (D. Del. Mar. 11, 2011) (Robinson, J.).
Redacted Sealed Letter to Mag J Thynge fr Shaw re Plaintiffs Mar. 3, 2011, dated Mar. 10, 2011.
Stipulation to Extend Time for Myland to Resp to Complaint, Civ. No. 11-164-SLR, dated Mar. 18, 2011.
Order Granting Stipulation to Extend Time, e-mail dated Mar. 22, 2011.
Substitution of Counsel, Civ. No. 1:11-cv-0164, dated Mar. 25, 2011.
Mylan Defendants Answer to Complaint w—Counterclaim, Civil Action No. 1:11-cv-0164 (SLR),dated Mar. 25, 2011.
Mylan Pharmaceuticals Disclosure Statement, Civil Action No. 1:11-cv-0164 (SLR),dated Mar. 25, 2011.
Mylan Inc. Disclosure Statement, Civil Action No. 1:11-cv-0164 (SLR),Mar. 25, 2011.
Order Setting Discovery Teleconference w—Judge Thynge, C. A. No. 10-123-SLR/MPT, dated Mar. 25, 2011.
Plaintiffs Notice of Service of Williams Rebuttal Expert Report, C. A. No. 10-123-SLR, dated Mar. 25, 2011.
Plaintiffs Motion to Stay—Proposed Order C. A. No. 10-123-SLR/MPT, dated Mar. 28, 2011.
Plaintiffs Motion to Stay, C. A. No. 10-123-SLR/MPT, dated Mar. 28, 2011.
Mylan Pro Hac Motion re Figg and Bhatt of Rothwell Figg, C. A. No. 11-0164-SLR, dated Mar. 29, 2011.
Sandoz Notice of Service of Polli Suppl and Rebuttal Expert Reports, C.A. No. 10-123-SLR, dated Mar. 29, 2011.
Letter to Mag J Thynge fr McCann encl courtesy copy of Mot to Stay, dated Mar. 29, 2011.
Letter to Mag J Thynge fr McCann encl courtesy copy of Mot to Stay, Civil Action No. 10-123-SLR-MPT, dated Mar. 28, 2011.
Redacted Letter to Mag J Thynge fr McCann re discovery extension—Proposed Order, C.A. No. 10-123-SLR/MPT, dated Mar. 29, 2011.
Redacted Letter to Mag J Thynge fr McCann re discovery extension, dated Mar. 28, 2011.

\* cited by examiner

TRANSMUCOSAL EFFERVESCENT

CROSS-REFERENCE TO RELATED APPLICATIONS

The present application is a continuation application of U.S. patent application Ser. No. 09/661,693, filed Sep. 14, 2000, which is a continuation of U.S. patent application Ser. No. 09/327,814, filed Jun. 8, 1999, now U.S. Pat. No. 6,200,604, which is a continuation application of U.S. patent application Ser. No. 09/277,424, filed Mar. 26, 1999, now abandoned, which claims priority from U.S. Provisional Application 60/079,652 filed Mar. 27, 1998.

BACKGROUND OF THE INVENTION

The present invention relates to pharmaceutical compositions, and more particularly to pharmaceutical compositions for oral administration of a medicament, which contain an effervescent agent for enhancing oral drug absorption across the buccal, sublingual, and gingival mucosa.

DESCRIPTION OF PRIOR ART

Effervescents have been shown to be useful and advantageous for oral administration. See Pharmaceutical Dosage Forms: Tablets Volume I, Second Edition. A. Leiberman. Ed. 1989, Marcel Dekker, Inc. As discussed in this text, and as commonly employed, an effervescent tablet is dissolved in water to provide a carbonated or sparkling liquid drink. See also U.S. Pat. Nos. 5,102,665 and 5,468,504 to Schaeffer, herein incorporated by reference. In such a drink, the effervescent helps to mask the taste of medicaments.

Effervescent compositions have also been employed for use as taste masking agents in dosage forms which are not dissolved in water prior to administration. For example, U.S. Pat. No. 4,639,368 describes a chewing gum containing a medicament capable of absorption through the buccal cavity and containing a taste masking amount of an effervescent.

More recently effervescents have been employed to obtain rapid dissolution and/or dispersion of the medicament in the oral cavity. See U.S. Pat. Nos. 5,178,878 and 5,223,264. The effervescent tends to stimulate saliva production thereby providing additional water to aid in further effervescent action. These dosage forms give an agreeable presentation of the drug, particularly for patients who have difficulty in swallowing tablets or capsules. PCT application WO 97/06786 describes pre-gastric absorption of certain drugs using rapidly-disbursing dosage forms.

Various proposals have been advanced for oral mucosal administration of various drugs. When drugs are absorbed from the oral mucosa, they bypass the gastrointestinal and hepatic metabolism process. This can lead to a faster onset of action and/or improved bioavailability of a drug. However, many compounds do not rapidly penetrate the oral mucosa. See, e.g., Christina Graffner, *Clinical Experience with Novel Buccal and Sublingual Administration*; NOVEL DRUG DELIVERY AND ITS THERAPEUTIC APPLICATION, edited by L. F. Prescott and W. S. Nimmo (1989); David Harris & Joseph R. Robinson, *Drug Delivery via the Mucous Membranes of the Oral Cavity*; JOURNAL OF PHARMACEUTICAL SCIENCES, Vol. 81 (January 1992); *Oral Mucosal Delivery*, edited by M. J. Rathbone, which are incorporated by reference. The compounds which may be well absorbed per-orally (through the gastrointestinal tract) may not be well absorbed through the mucosa of the mouth because the oral mucosa is less permeable than the intestinal mucosa and it does not offer as big a surface area as the small intestine.

Despite these and other efforts toward increasing the permeation of medicaments across the oral mucosa, there have been unmet needs for improved methods of administrating medicaments across the oral mucosa.

SUMMARY OF THE INVENTION

The pharmaceutical compositions of the present invention comprise an orally administerable medicament in combination with an effervescent agent used as penetration enhancer to influence the permeability of the medicament across the buccal, sublingual, and gingival mucosa.

DETAILED DESCRIPTION OF THE INVENTION

One aspect of this invention is to use effervescents as penetration enhancers for influencing oral drug absorption. Effervescent agents can be used alone or in combination with other penetration enhancers, which leads to an increase in the rate and extent of absorption of an active drug. It is believed that such increase can arise from one or all of the following mechanisms:
1. reducing the mucosal layer thickness and/or viscosity;
2. tight junction alteration;
3. inducing a change in the cell membrane structure; and
4. increasing the hydrophobic environment within the cellular membrane.

The present dosage forms should include an amount of an effervescent agent effective to aid in penetration of the drug across the oral mucosa. Preferably, the effervescent is provided in an amount of between about 5% and about 95% by weight, based on the weight of the finished tablet, and more preferably in an amount of between about 30% and about 80% by weight. It is particularly preferred that sufficient effervescent material be provided such that the evolved gas is more than about 5 $cm^3$ but less than about 30 $cm^3$, upon exposure of the tablet to an aqueous environment. However, the amount of effervescent agent must be optimized for each specific drug.

The term "effervescent agent" includes compounds which evolve gas. The preferred effervescent agents evolve gas by means of a chemical reaction which takes place upon exposure of the effervescent agent (an effervescent couple) to water and/or to saliva in the mouth. This reaction is most often the result of the reaction of a soluble acid source and a source of carbon dioxide such as an alkaline carbonate or bicarbonate. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, malic, fumeric, adipic, and succinic. Carbonate sources include dry solid carbonate and bicarbonate salts such as, preferably, sodium bicarbonate, sodium carbonate, potassium bicarbonate and potassium carbonate, magnesium carbonate and the like. Reactants which evolve oxygen or other gasses and which are safe for human consumption are also included.

The effervescent agent(s) of the present invention is not always based upon a reaction which forms carbon dioxide. Reactants which evolve oxygen or other gasses which are safe for human consumption are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

The present dosage forms may also include in amounts additional to that required for effervescence a pH adjusting substance. For drugs that are weakly acidic or weakly basic, the pH of the aqueous environment can influence the relative concentrations of the ionized and unionized forms of the drug present in solution according to the Henderson-Hasselbach equation. The pH of solutions in which an effervescent couple has dissolved is slightly acidic due to the evolution of carbon dioxide. The pH of the local environment, e.g., saliva in immediate contact with the tablet and any drug that may have dissolved from it, may be adjusted by incorporating in the tablet a pH adjusting substances which permit the relative portions of the ionized and unionized forms of the drug to be controlled. In this way, the present dosage forms can be optimized for each specific drug. If the unionized drug is known or suspected to be absorbed through the cell membrane (transcellular absorption) it would be preferable to alter the pH of the local environment (within the limits tolerable to the subject) to a level that favors the unionized form of the drug. Conversely, if the ionized form is more readily dissolved the local environment should favor ionization.

The aqueous solubility of the drug should preferably not be compromised by the effervescent and pH adjusting substance, such that the dosage forms permit a sufficient concentration of the drug to be present in the unionized form The percentage of the pH adjusting substance and/or effervescent should therefore be adjusted depending on the drug.

Suitable pH adjusting substance for use in the present invention include any weak acid or weak base in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The active ingredient suitable for use in the present dosage forms can include systematically distributable pharmaceutical ingredients, vitamins, minerals, dietary supplements, as well as non-systematically distributable drugs. Preferably, the active ingredient is a systemically active pharmaceutical ingredient which is absorbable by the body through the oral mucosa. Although the dosage forms can be employed with a wide range of drugs, as discussed below, it is especially suitable for drugs and other pharmaceutical ingredients which suffer significant loss of activity in the lumen of the gastrointestinal tract or in the tissues of the gastrointestinal tract during absorption process or upon passage through the liver after absorption in the intestinal tract. Absorption through the oral mucosa allows the drug to enter the systemic circulation without first passing through the liver, and thus alleviates the loss of activity upon passage through the liver.

Pharmaceutical ingredients may include, without limitation, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers; peptides, proteins, oligonucleotides and other substances of biological origin, and combinations thereof. Also encompassed by the terms "active ingredients(s)", "pharmaceutical ingredient(s)" and "active agents" are the drugs and pharmaceutically active ingredients described in Mantelle, U.S. Pat. No. 5,234,957, in columns 18 through 21. That text of Mantelle is hereby incorporated by reference. Alternatively or additionally, the active ingredient can include drugs and other pharmaceutical ingredients, vitamins, minerals and dietary supplements as the same are defined in U.S. Pat. No. 5,178,878, the disclosure of which is also incorporated by reference herein.

The dosage form preferably includes an effervescent couple, in combination with the other ingredients to enhance the absorption of the pharmaceutical ingredient across the oral mucosa and to improve the disintegration profile and the organoleptic properties of the dosage form. For example, the area of contact between the dosage form and the oral mucosa, and the residence time of the dosage form in the oral cavity can be improved by including a bioadhesive polymer in this drug delivery system. See, e.g., *Mechanistic Studies on Effervescent-Induced Permeability Enhancement* by Jonathan Eichman (1997), which is incorporated by reference herein. Effervescence, due to its mucus stripping properties, would also enhance the residence time of the bioadhesive, thereby increasing the residence time for the drug absorption. Non-limiting examples of bioadhesives used in the present invention include, for example, Carbopol 934 P, Na CMC, Methocel, Polycarbophil (Noveon AA-1), HPMC, Na alginate, Na hyaluronate and other natural or synthetic bioadhesives.

In addition to the effervescence-producing agents, a dosage form according to the present invention may also include suitable non-effervescent disintegration agents. Non-limiting examples of non-effervescent disintegration agents include: microcrystalline, cellulose, croscarmelose sodium, crospovidone, starches, corn starch, potato starch and modified starches thereof, sweeteners, clays, such as bentonite, alginates, gums such as agar, guar, locust bean, karaya, pecitin and tragacanth. Disintegrants may comprise up to about 20 weight percent and preferably between about 2 and about 10% of the total weight of the composition.

In addition to the particles in accordance with the present invention, the dosage forms may also include glidants, lubricants, binders, sweeteners, flavoring and coloring components. Any conventional sweetener or flavoring component may be used. Combinations of sweeteners, flavoring components, or sweeteners and flavoring components may likewise be used.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Coloring agents may include titanium dioxide, and dyes suitable for food such as those known as F.D. & C. dyes and natural coloring agents such as grape skin extract, beet red powder, beta-carotene, annatto, carmine, turmeric, paprika, etc. The amount of coloring used may range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an mount ranging from about 0.05 to about 3 percent by weight based upon the weight of the composition. Particularly preferred flavors are the grape and cherry flavors and citrus flavors such as orange.

One aspect of the invention provides a solid, oral tablet dosage form suitable for sublingual, buccal, and gingival administration. Excipient fillers can be used to facilitate tableting. The filler desirably will also assist in the rapid dissolution of the dosage form in the mouth. Non-limiting examples of suitable fillers include: mannitol, dextrose, lactose, sucrose, and calcium carbonate.

Method of Manufacture

Tablets can either be manufactured by direct compression, wet granulation or any other tablet manufacturing technique. See, e.g., U.S. Pat. Nos. 5,178,878 and 5,223,264, which are incorporated by reference herein. The tablet may be a layered tablet consisting of a layer of the active ingredient sandwiched between a bioadhesive layer and an effervescence layer. Other layered forms which include the ingredients set forth above in layers of diverse compositions.

| | |
|---|---|
| Effervescence Level: | Between 5%-95% |
| Tablet Size: | Between 3/16"-5/8" |
| Tablet Hardness | Between 5N and 80N |
| Route of Administration | Sublingual, Buccal, Gingival |

The dosage form may be administered to a human or other mammalian subject by placing the dosage form in the subject's mouth and holding it in the mouth, either adjacent a cheek (for buccal administration), beneath the tongue (for sublingual administration) and between the upper lip and gum (for gingival administration). The dosage form spontaneously begins to disintegrate due to the moisture in the mouth. The disintegration, and particularly the effervescence, stimulates additional salivation which further enhances disintegration.

EXAMPLE 1

The dosage form should include Fentanyl, an effervescent and pH adjusting substance so that the pH is adjusted to neutral (or slightly higher) since the pKa of fentanyl is 7.3. At this pH, the aqueous solubility of this poorly water-soluble drug would not be compromised unduly, and would permit a sufficient concentration of the drug to be present in the unionized form.

Two fentanyl formulations, each containing 36% effervescence, were produced. These tablets were compressed using half-inch shallow concave punches.

| FORMULATION | COMPONENT | QUANTITY (MG) |
|---|---|---|
| SHORT DISINTEGRATION TIME | Fentanyl, citrate, USP | 1.57 |
| | Lactose monohydrate | 119.47 |
| | Microcrystalline Cellulose | 119.47 |
| | Sodium carbonate, anhydrous | 46.99 |
| | Sodium bicarbonate | 105 |
| | Citric acid, anhydrous | 75 |
| | Polyvinylpyrrolidone, Cross-linked | 25 |
| | Magnesium stearate | 5 |
| | Colloidal silicon dioxide | 2.5 |
| | Total tablet mass | 500 |
| LONG DISINTEGRATION TIME | Fentanyl citrate, USP | 1.57 |
| | Lactose monohydrate | 270.93 |
| | Sodium carbonate, anhydrous | 40.00 |
| | Sodium bicarbonate | 105 |
| | Citric acid, anhydrous | 75 |
| | Magnesium stearate | 5 |
| | Colloidal silicon dioxide | 2.5 |
| | Total tablet mass | 500 |

EXAMPLE 2

The dosage form included prochlorperazine (pKa=8.1), and effervescent and pH adjusting substance so that a slightly higher pH is produced to facilitate the permeation enhancement.

With respect to prochlorperazine, an anti-emetic drug, two formulations, buccal and sublingual, were developed. The buccal tablets were compressed as quarter inch diameter biconvex tablets, whereas the sublingual tablets were three-eighths inch diameter biconvex tablets. These dimensions were chosen to give a comfortable fit in the respective part of the oral cavity for which they were designed. The formulae for these tablets are as follows:

| FORMULATION | COMPONENT | QUANTITY (MG) |
|---|---|---|
| BUCCAL | Prochlorperazine | 5.00 |
| | Sodium Bicarbonate | 15.52 |
| | Citric Acid, Anhydrous | 11.08 |
| | Sodium Bicarbonate | 45.78 |
| | HPMC K4M Prem | 5.00 |
| | Dicalcium phosphate dihydrate | 5.00 |
| | Mannitol | 11.67 |
| | Magnesium Stearate | 0.95 |
| | Total | 100.00 |
| SUBLINGUAL | Prochlorperazine | 5.00 |
| | Sodium Bicarbonate | 61.25 |
| | Citric Acid, Anhydrous | 43.75 |
| | Sodium Bicarbonate | 95 |
| | Sodium carbonate | 91.25 |
| | HPMC Methocel K4M Prem | 40 |
| | Mannitol | 60 |
| | Magnesium Stearate | 3.75 |
| | TOTAL | 400 |

What is claimed is:

1. A tablet comprising:

a) fentanyl and/or at least one pharmaceutically acceptable salt thereof in a pharmaceutically effective amount for buccal mucosal administration in a human;

b) at least one effervescent couple present in an amount ranging from about 5% by weight to about 80% by weight based on the weight of the tablet, said effervescent couple comprising at least one acid and at least one base, wherein said at least one base, which may be the same as or different from said at least one pH adjusting base, is present in an amount required for effervescence, wherein the at least one acid is selected from citric, tartaric, malic, fumaric, adipic and succinic acid, and the at least one base is selected from sodium bicarbonate, sodium carbonate, potassium bicarbonate, potassium carbonate and magnesium carbonate; and c) at least one pH adjusting base, selected from sodium carbonate, potassium carbonate, magnesium carbonate, disodium hydrogen phosphate, sodium dihydrogen phosphate, dipotassium hydrogen phosphate, and potassium dihydrogen phosphate, said pH adjusting base being present in an amount additional to that required for effervescence; and wherein said tablet further comprises at least one disintegration agent present in an amount up to about 20% by weight based on the weight of the tablet.

2. The tablet according to claim 1, wherein said at least one disintegration agent is chosen from microcrystalline cellulose, croscarmelose sodium, crospovidone, starches, modified starches, sweeteners, clays, alginates, and gums.

3. The tablet according to claim 1, wherein the at least one disintegration agent is present in an amount ranging from 2% by weight to about 10% by weight based on the weight of the tablet.

4. The tablet according to claim 1, further comprising at least one additional component chosen from glidants, lubricants, binders, sweeteners, flavoring components, and coloring components.

5. The tablet according to claim 1, further comprising at least one bioadhesive.

6. The tablet according to claim 1, comprising fentanyl citrate.

7. A tablet according to claim 1, wherein: the at least one pH adjusting substance comprises sodium carbonate; at least one acid in the at least one effervescent couple comprises citric acid; and the at least one base in the at least one effervescent couple comprises sodium bicarbonate; and wherein the at least one disintegration agent comprises at least one modified starch.

* * * * *